United States Patent [19]
Ackermann et al.

[11] 4,117,238
[45] Sep. 26, 1978

[54] PROCESS FOR THE TRANS-ESTERIFICATION OF ACRYLIC AND METHACRYLIC ESTERS

[75] Inventors: Rolf Ackermann, Hanau; Wilfried Felber, Gross-Welzheim; Gerhard Morlock, Hanau, all of Germany

[73] Assignee: Deutsche Gold-und Silber-Scheideanstalt vormals Roessler, Frankfurt am Main, Germany

[21] Appl. No.: 693,596

[22] Filed: Jun. 7, 1976

[30] Foreign Application Priority Data
Jun. 5, 1975 [DE] Fed. Rep. of Germany ....... 2524930

[51] Int. Cl.$^2$ .................... C07C 69/54; C07C 67/03
[52] U.S. Cl. .................................................. 560/217
[58] Field of Search .................................. 260/486 R

[56] References Cited
U.S. PATENT DOCUMENTS
3,887,609   4/1974   Strehlke et al. ................ 260/486 R OTHER PUBLICATIONS
Mori, K. et al., "A Mild Transesterification Method," *Synthesis*, No. 12, 1973, pp. 790-791.

*Primary Examiner*—Donald G. Daus
*Assistant Examiner*—Lisa Jones
*Attorney, Agent, or Firm*—Beveridge, DeGrandi, Kline & Lunsford

[57] ABSTRACT

An improved process for the trans-esterification of esters of acrylic or methacrylic acid in the presence of a trans-esterification catalyst and a polymerization inhibitor includes the use of about 0.05 to about 10% by weight of an alkali metal cyanide as the catalyst.

3 Claims, No Drawings

PROCESS FOR THE TRANS-ESTERIFICATION OF ACRYLIC AND METHACRYLIC ESTERS

This invention relates to a process for the trans-esterification of esters of acrylic or methacrylic acid in the presence of a trans-esterification catalyst and a polymerization inhibitor. More particularly, this invention relates to an improved process for the trans-esterification of such esters, wherein the catalyst is an alkali metal cyanide.

It is known in the art that acid and basic catalysts can be used in the trans-esterification of acrylic or methacrylic acid esters. The acid catalysts, such as sulfuric acid or p-toluene sulphonic acid, exhibit only slight activity and frequently lead to secondary reactions. (Journal of Applied Chemistry, Vol. 13, 1963, pp. 168–171). Basic catalysts exhibit greater activity; for example, the alkali alcoholates are most frequently described. (Swiss Pat. No. 239,750). Basic catalysts, however, accelerate the addition of alcohols to the double bonds of unsaturated carboxylic acids, which leads to the formation of alcoxy carboxylic acid esters. As a result, the yields are correspondingly lowered, and the reactions must be terminated after reaching low conversions.

These disadvantages can be avoided when a titanium acid ester is used as the catalyst. (See U.S. Pat. No. 2,822,348). For this reason, titanium acid esters are predominantly used in trans-esterification operations on an industrial scale. The titanium esters, however, do have the disadvantage that after the reaction, they must be hydrolyzed into insoluble substances before they can be separated from the reaction mixture. This can be accomplished by treatment with caustic soda. Moreover, the titanium acid esters are not universally applicable to trans-esterification reactions. For example, they are poor catalysts for the trans-esterification of methylmethacrylate with glycols, such as ethylene glycol, and only very low conversions are obtained.

It is also known in the art that magnesium alcoholates can be used as trans-esterification catalysts (German AS 1 568 376). These catalysts make it possible to achieve high yields. They also catalyze the trans-esterification of methylmethacrylate with glycols. Since they are present in a heterogeneous phase at the end of the trans-esterification reaction, they can easily be separated from the reaction mixture. The magnesium alcoholates, however, are hydrolyzed by small quantities of moisture into substances which are no longer catalytically effective. Therefore, the magnesium alcoholates require strictly anhydrous reaction conditions.

Accordingly, this invention provides an improved process for the trans-esterification of esters of acrylic or methacrylic acid in the presence of a trans-esterification catalyst and a polymerization inhibitor. In the improvement provided by this invention, the trans-esterification catalyst is at least one alkali metal cyanide, which is employed in an amount of about 0.05 to about 10% by weight, related to the total weight of reactants. In a preferred embodiment of this invention, the alkali metal cyanide is employed in an amount of about 0.1 to about 2% by weight, related to the total weight of the reactants. The preferred alkali metal cyanide is potassium cyanide.

Alkali metal cyanides are hardly soluble in esters of acrylic or methacrylic acids, such as methylmethacrylate. It has surprisingly been found, however, that they catalyze the trans-esterification of such esters in a heterogeneous phase, and they make it possible to achieve high yields. Additionally, they have been found to be particularly effective in the trans-esterification of such esters with glycols. The trans-esterification in the presence of alkali metal cyanides takes place considerably more rapidly than potential secondary reactions, such as the addition of alcohols to the double bonds or the formation of dimers or trimers from glycols, or the addition of the alkali metal cyanide to the double bond.

It has been found that the use of the alkali metal cyanides makes it possible to employ technical grade (industrial purity) alcohols or glycols, which possibly contain water. The ability to employ technical grade reactants is of particular advantage. Unlike the titanates and magnesium alcoholates described hitherto, the cyanides are not hydrolyzed by water, which would otherwise render them ineffective. Therefore, when the cyanides are employed as the catalysts it is not necessary to dehydrate the reaction mixture prior to addition of the catalyst thereto. It will be understood, however, that in special cases dehydration can be carried out, for example, for the improvement of the yield. Additionally, the insensitivity of the catalyst to water is especially advantageous because the alcohol can be added during the course of the reaction. As a result, it is possible to maintain a low concentration of alcohol in the reaction mixture, and thereby avoid secondary reactions to an even greater extent. For example, when the alcohol is ethylene glycol, self-condensation of the alcohol can be avoided.

The trans-esterification catalyst employed in this invention can be easily separated from the reaction mixture. For example, one can employ simple filtration. As a result, processing is considerably simplified. There is no need to hydrolyze the catalysts prior to separation or to render them insoluble and thus unusable by some other measures.

Generally, the esters of acrylic or methacrylic acid with methanol or ethanol are employed as starting materials in the process of this invention.

Particularly good results are achieved in the trans-esterification of methylmethacrylate into other esters of methacrylic acid.

The trans-esterification can take place with practically any alcohol; however, the ester of acrylic or methacrylic acid and the alcoholic component should be at least partially miscible with one another under the reaction conditions. Typical of the alcohols that can be employed are monovalent primary, straight chain or branched aliphatic alcohols, such as $C_3$ to $C_{20}$ alcohols, for example, n-propanol, n-butanol, iso-butanol, lauryl alcohol, stearyl alcohol, 2-ethylhexanol; multivalent aliphatic alcohols, especially ethylene glycol, diethylene glycol, triethylene glycol, neopentyl glycol, trimethylolpropane; cycloaliphatic alcohols, such as cyclohexanol; aromatic alcohols, such as benzyl alcohol; alcohols containing other functional groups, such as ether alcohols, for example, ethylene glycol monomethyl ether, or amino alcohols, such as dimethylamino ethanol.

The process of this invention is carried out in the presence of at least one inhibitor for radical polymerizations. Such inhibitors are well-known in the art. Typical of the inhibitors that can be employed in the process of this invention are hydroquinone, hydroquinone monomethyl ether, tertiary butyl pyrocatechin, other mono- or multivalent phenols, quinones, aminophenols and aromatic amines, such as diphenyl amine, phenyl-β-naphthylamine, or quinone dyes, such as methylene blue. The inhibitors are effectively employed in quantities between about 100 and about 1000 ppm, related to the total weight of the reactants.

The trans-esterification is carried out in such a way that the ester of acrylic or methacrylic acid in a mole ratio between about 2 : 1 and about 6 : 1 in relation to one OH equivalent of the alcohol that is to be reacted and together with said alcohol or a part of the total quantity of the alcohol and at least one inhibitor and the required quantity of the at least one alkali metal cyanide, is heated in an appropriately dimensioned vessel provided with a column, preferably by conducting air through for better stabilization. The alcohols can be employed in their industrial grade; for an increase in yield, the mixture of the ester of acrylic or methacrylic acid, alcohol and at least one inhibitor can be dehydrated by azeotropic distillation prior to the addition of the alkali metal cyanide.

It is advantageous during the reaction to dose in 100 ml of starting ester per approximately one liter of reaction mixture at the upper end of the column, which ester is stabilized with the same inhibitor in the same concentration as the sump. This mode of operation prevents the polymerization of the distilled-off ester of acrylic or methacrylic acid in the column.

The reaction mixture is heated with total reflux in the column until the azeotropic temperature of the starting ester of acrylic or methacrylic acid is obtained with the liberated alcohol at the head of the column. (The azeotropic temperature lies, for example, in the case of trans-esterification of methylmethacrylate at 65° C., the azeotropic composition at 84.5% methanol and 15.5% methylmethacrylate). After that, the azeotrope at the head of the column is removed. If at the start only a portion of the total quantity of alcohol was added to the reaction mixture, then the remainder can be dosed in continuously or added in small fractions. After three to five hours, the temperature at the head of the column rises to the boiling temperature of the excess acrylic or methacrylic acid ester employed, and the reaction is then complete. The quantity of alcohol reacted can be measured by extracting the distilled-off azeotrope from the ester of acrylic or methacrylic acid and from its alcohol component with water, and by weighing the water insoluble residue, or by gas chromatographic determination of the composition of the azeotrope. After cooling of the reaction vessel, the sump is filtered off from the alkali metal cyanide. The surplus of the ester of acrylic or methacrylic acid employed is removed by distillation under vacuum.

The residue is generally sufficiently pure and especially free of polymers. It can be used as such insofar as the inhibitor contained therein is not objectionable. It can also be purified by way of known processes, and it can be freed of the inhibitor, for example, by washing, filtering with activated charcoal, or by distillation when the ester has sufficient volatility. The yields of the desired ester lie generally between about 80% and about 100%.

The following Examples illustrate the process of this invention. All parts, proportions, ratios and percentages are by weight, unless otherwise indicated.

EXAMPLE 1

400 g of methyl methacrylate (4 mole), 148 g of n-butanol (2 mole), 2.74 g of potassium cyanide (0.5%) and 0.137 g of hydroquinone monomethyl ether (250 ppm) are added to a 1 liter round-bottomed flask. The batch is heated to approximately 75° C. by conducting air through, and at a temperature of 65° C. at the head of the column, the methyl methacrylate/methanol-azeotrope is distilled-off by way of a 1 m vigreux column. After 4 hours, the trans-esterification is finished. After cooling of the flask, the sump is filtered to remove the potassium cyanide, and the filter residue is washed with a little methyl methacrylate. The filtrate is concentrated at 40° C. under a water jet vacuum. There results a residue of n-butyl methacrylate of 280 g $\triangleq$ 98.5%. The n-butyl methacrylate thus obtained can be used without any further processing.

EXAMPLE 2

500 g of ethylacrylate (5 mole), 92.5 g of n-butanol (1.25 mole) and 0.148 g of hydroquinone (250 ppm) are added to a 1 liter round-bottomed flask. By conducting air through by way of a 1 m vigreux column, the azeotrope is dehydrated. After cooling of the contents of the flask to 60° to 70° C., 6 g of potassium cyanide (1%) are added, and the ethylacrylate/ethanol-azeotrope is distilled-off at 77° C. at the head of the column. After 4 to 5 hours, the trans-esterification is completed. After cooling down of the flask, the potassium cyanide is filtered off and the filter residue is washed out with a little ethyl acrylate. The filtrate is processed by fractional distillation. 155 g of n-butyl acrylate $\triangleq$ 97% are obtained.

EXAMPLE 3

300 g of methyl methacrylate (3 mole), 135 g of stearyl alcohol (0.5 mole), 4.35 g of KCN (1%) and 0.108 g of hydroquinone methyl ether (250 ppm) are added to a 1 liter round-bottomed flask. The mixture is heated to about 75° C. by conducting air through it and the methyl methacrylate/methanol-azeotrope is removed at a temperature of 65° C. at the head of the column by way of a 1 m vigreux column. The trans-esterification is completed after 3.5 hours. After cooling down of the flask, the sump is filtered to remove the potassium cyanide, and the filter residue is washed with a little methyl methacrylate. The filtrate is concentrated at 40° C. under a water jet vacuum. A white, crystalline residue of stearyl methacrylate of 162 g $\triangleq$ 96% will result.

EXAMPLE 4

1200 g of methyl methacrylate (12 mole), 156 g of neopentyl glycol (1.5 mole), 6.7 g of KCN (0.5%) and 0.34 g of hydroquinone monomethyl ether (250 ppm) are added to a 2 liter round-bottomed flask. The mixture is heated to about 75° C., and at a temperature of 65° C. at the head of the column, the methyl methacrylate/methanol-azeotrope is distilled off via a 1 m vigreux column. The trans-esterification is completed after 3.5 hours. After cooling of the flask, the sump is filtered to remove the potassium cyanide, and the filter residue is washed with a little methyl methacrylate. The filtrate is concentrated at 40° C. under water jet vacuum. A residue of neopentyl-bis-methacrylate of 356 g $\triangleq$ 89% will result. The neopentyl-bis-methacrylate thus obtained can be used further either without any further processing or optionally after destabilization.

EXAMPLE 5

400 g of methyl methacrylate (4 mole), 200 g of cyclohexanol (2 mole) and 0.30 g of N,N'-diphenylbenzidine (500 ppm) are added to a 1 liter round-bottomed flask. Azeotropic dehydration is accomplished by conducting air through the resulting mixture, by way of a 1 m vigreux column. After cooling of the contents of the flask to about 75° C., 3 g of potassium cyanide (0.5%) are added, and the methyl methacrylate/methanol-azeotrope is distilled-off at a temperature of 65° C. at the head of the column. The trans-esterification is completed after 3.5 hours. After cooling of the flask, the sump is filtered to remove the potassium cyanide, and the filter residue is washed with a little methyl methacrylate. The filtrate is concentrated at 40° C. under a water jet vacuum. A residue of cyclohexyl methacrylate of 310 g $\triangleq$ 85% will result.

EXAMPLE 6

400 g of methyl methacrylate (4 mole), 152 g of ethylene glycol monomethyl ether (2 mole), 2.75 g of KCN (0.5%) and 0.14 g of hydroquinone monomethyl ether (250 ppm) are added to a 1 liter round-bottomed flask. The batch is heated to about 75° C. and the methyl methacrylate/methanol-azeotrope is distilled-off by way of a 1 m vigreux column at 65° C. temperature at the head of the column. After 4 hours, the trans-esterification is completed. After cooling of the flask, the sump is filtered to remove the potassium cyanide, and the filter residue is washed with a little methyl methacrylate. The filtrate is concentrated at 40° C. under a water jet vacuum. A residue of ethylene glycol monomethyl-ether methacrylate of 260 g $\triangleq$ 90% results.

EXAMPLE 7

1200 g of methyl methacrylate (12 mole), 20 g of ethylene glycol and 0.65 g of N,N'-diphenyl benzidine (500 ppm) are added to a 2 liter round-bottomed flask. After the addition of 12.9 g of potassium cyanide (1%), a quantity of methanol equivalent to the ethylene glycol employed is taken off as methyl methacrylate/methanol-azeotrope while conducting air through at a temperature of 65° C. at the head of the column (approximately ½ hour). After that, an additional 73g of ethylene glycol are dosed in within 2 hours (total quantity of ethylene glycol 93g=1.5 mole). After altogether 4.5 hours of removing azeotrope, the trans-esterification is completed. After cooling of the flask, the sump is filtered to remove the potassium cyanide, and the filter residue is washed with a little methyl methacrylate. The filtrate is concentrated at 40° C. under a water jet vacuum. A residue of ethylene glycol dimethacrylate of 286 g = 96.5% results. The ethylene glycol dimethacrylate obtained in such a way can be used either without any further processing or optionally after destabilization.

While potassium cyanide has been indicated to be the preferred alkali metal cyanide, one can employ the alkali metal cyanides generally, for example, sodium and lithium cyanide. It will be understood that mixtures of catalysts can be employed. In practicing the process of this invention, the preferred esters of acrylic and methacrylic acid employed as reactants are the $C_1$–$C_4$ alkyl esters.

What is claimed is:

1. An improved process for the trans-esterification of esters of acrylic or methacrylic acid in the presence of a trans-esterification catalyst and a polymerization inhibitor, the improvement wherein said catalyst is at least one alkali metal cyanide, and said alkali metal cyanide is employed in an amount of about 0.05 to about 10 percent by weight, related to total weight of reactants.

2. Process according to claim 1 wherein said amount of said alkali metal cyanide is about 0.1 to about 2 percent by weight.

3. Process according to claim 1 wherein said alkali metal cyanide is potassium cyanide.

* * * * *